(12) United States Patent
Wu

(10) Patent No.: US 8,092,111 B2
(45) Date of Patent: Jan. 10, 2012

(54) FOLDING MECHANISM FOR JOINT

(76) Inventor: Sung-Tsun Wu, Pan Chiao (TW)

( * ) Notice: Subject to any disclaimer, the term of this patent is extended or adjusted under 35 U.S.C. 154(b) by 243 days.

(21) Appl. No.: 12/686,143

(22) Filed: Jan. 12, 2010

(65) Prior Publication Data
US 2010/0209179 A1 Aug. 19, 2010

(30) Foreign Application Priority Data
Feb. 18, 2009 (TW) ................................ 98202349 U

(51) Int. Cl.
*F16D 3/00* (2006.01)

(52) U.S. Cl. .......................................... 403/102; 280/642

(58) Field of Classification Search .................. 16/319, 16/321, 323, 324, 326, 349, 231, 437, 438, 16/408; 280/642, 647, 650, 658; 403/109.7, 403/109.8, 109.3, 109.6, 109.2, 109.1, 102, 403/322.3, 91, 92, 94, 95, 111; 135/114, 135/120.1, 120.2, 74; 74/551.3–551.7
See application file for complete search history.

(56) References Cited

U.S. PATENT DOCUMENTS
7,543,840 B2 * 6/2009 Lin ................................ 280/639

* cited by examiner

*Primary Examiner* — Daniel Stodola
*Assistant Examiner* — Daniel Wiley
(74) *Attorney, Agent, or Firm* — Muncy, Geissler, Olds & Lowe, PLLC

(57) ABSTRACT

A folding mechanism for a joint includes a first pivot unit, a second pivot unit, a locking unit and an operation unit. The operation unit drives the locking unit to control the first pivot unit and the second pivot unit to be locked together or released to rotate.

9 Claims, 5 Drawing Sheets

FOLDING MECHANISM FOR JOINT

BACKGROUND OF THE INVENTION

1. Field of the Invention

The present invention relates generally to a joint, and in particular to a folding mechanism for the joint.

2. The Prior Arts

Most of the baby strollers have folding mechanisms for the convenience of carry and storage. The baby sits in the baby stroller such that the parents do not need to hold the baby. When the baby stroller is not in use, the users operate the folding mechanism to fold the baby stroller and put the folded baby stroller in the car trunk or the storage room.

However, the operation members of the conventional folding mechanism for baby strollers are usually located close to the joint so that the users have to bend their body to touch and operate the operation members when folding the baby stroller. It is inconvenient for the users. Besides, the operation members can be accidentally touched and activated by the baby in the stroller, which will injure the baby. It is a serious safety issue.

SUMMARY OF THE INVENTION

A primary objective of the present invention is to provide a folding mechanism for a joint that overcomes the disadvantages of the conventional designs.

Another objective of the present invention is to provide a folding mechanism for a joint that is structurally simple, low cost, secured, safe and easy to use.

A folding mechanism for a joint according to the present invention includes a first pivot unit, a second pivot unit, a locking unit and an operation unit. The first pivot unit has a first tube connected with a first pivot member. An axle is extended from the first pivot member and a frame having an aperture is connected to the first pivot member. The second pivot unit has a second tube connected with a second pivot member and the second tube has a passage defined therethrough. A slot is defined through a wall of the second tube in the longitudinal direction. A tubular member is connected to the second pivot member and has a reception hole in which the axle is inserted. The second pivot member includes an insertion hole corresponding to the aperture. The locking unit has a pin and an elastic member. One end of the pin includes a shank having a fixing end and the other end of the pin includes a curved surface. The elastic member is mounted to the shank and the pin passes through the aperture and the insertion hole. The operation unit has a sleeve having a sleeve hole in which the tubular member is rotatably inserted. The sleeve has a first arm and a second arm extending radially therefrom in two different angles. The first arm has a first fixed end at a distal end thereof and a pulling member has a first end thereof fixed with the first fixed end. A second end of the pulling member extends through the passage of the second pivot unit and is connected with an operation member which is movably engaged with the slot. The second arm has a second fixed end at a distal end thereof and the fixing end of the pin is fixed to the second fixed end of the second arm.

When the folding mechanism is used on a baby stroller, the user operates the operation member within the slot and the sleeve is rotated by the pulling member, the pin connected with the second arm is lowered to disengage from the aperture. Thus, the first and second pivot units are no longer locked by the locking unit. The baby stroller is then able to be folded. When unfolding the baby stroller, the first and second pivot units are pivoted to allow the aperture and the insertion hole to be in alignment with each other, the curved surface of the pin moves along the frame until the elastic member pushes the pin to insert into the aperture to lock the first and second pivot units.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
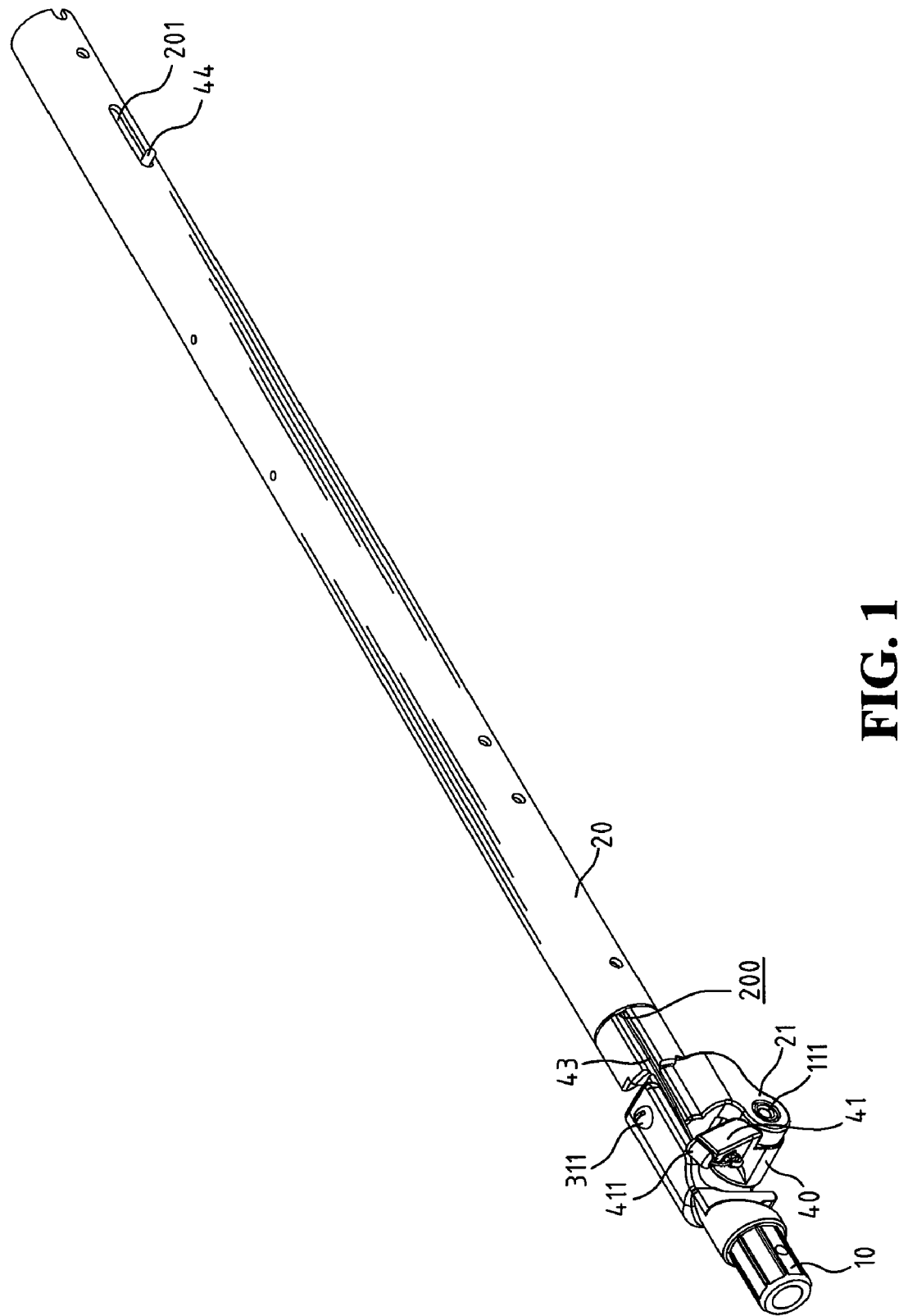
FIG. 1 is a perspective view showing a folding mechanism in accordance with the present invention.
Figure 2:
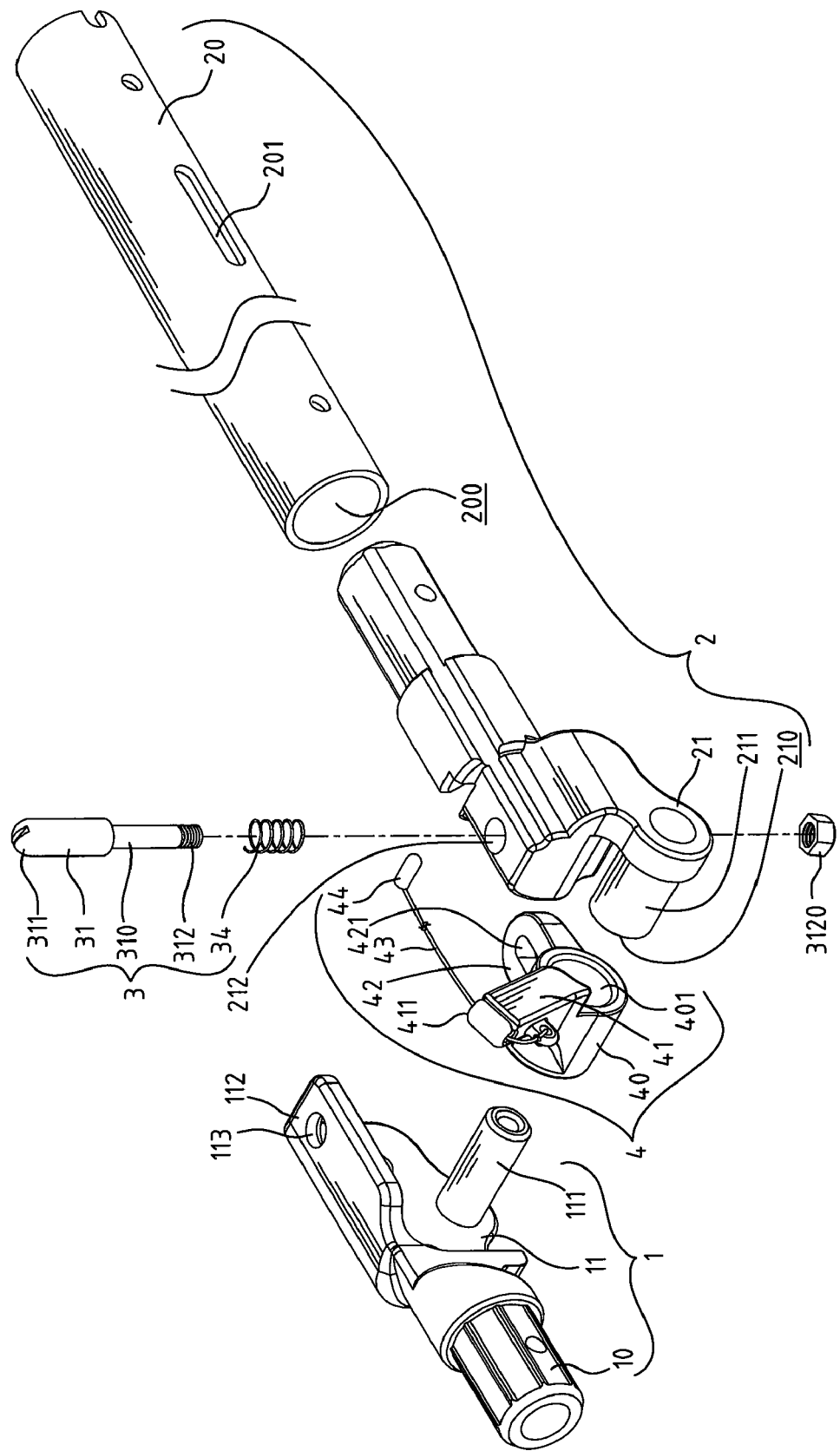
FIG. 2 is an exploded view showing the folding mechanism in accordance with the present invention.
Figure 3:
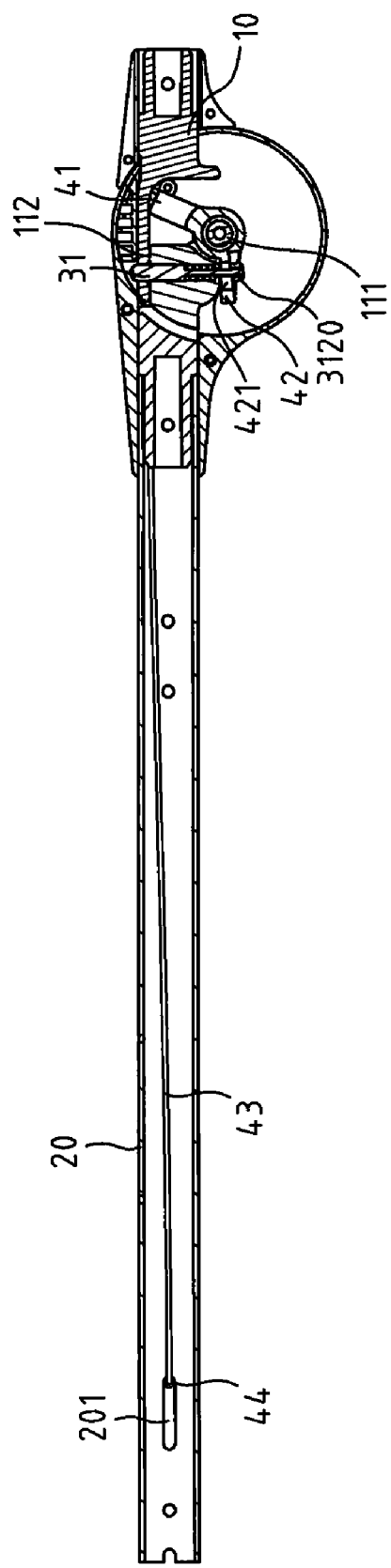
FIG. 3 is a cross sectional view showing the folding mechanism in accordance with the present invention.
Figure 5:
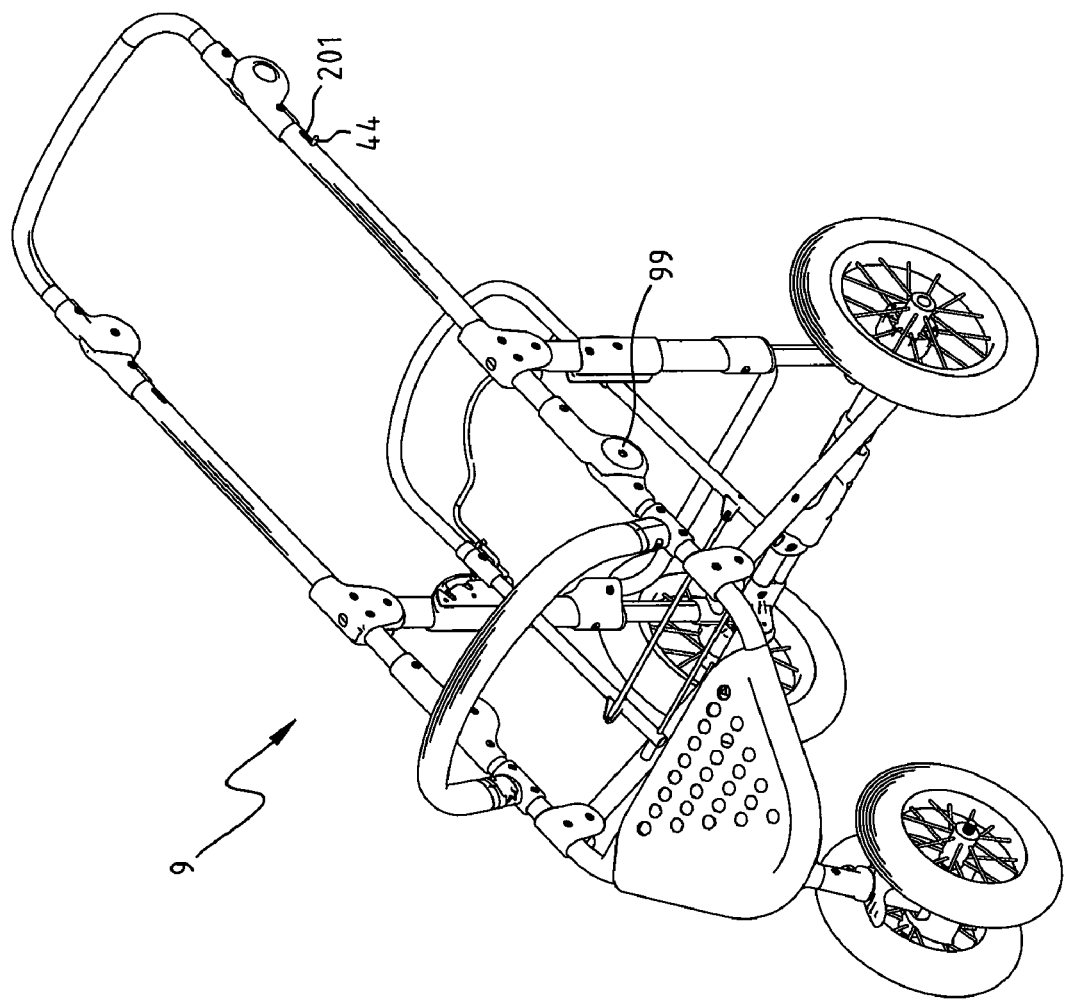
FIG. 5 shows that the folding mechanism according to the present invention is used on a baby stroller.

With reference to the drawings and in particular to FIGS. 1 to 3, a folding mechanism for a joint in accordance with an embodiment of the present invention includes a first pivot unit 1, a second pivot unit 2, a locking unit 3 and an operation unit 4. The first pivot unit 1 comprises a first tube 10 and a first pivot member 11 connected with the first tube 10. The first pivot member 11 has an axle 111 and a frame 112 extended therefrom. The frame 112 is in a plate shape and has an aperture 113. The second pivot unit 2 has a second pivot member 21 and a second tube 20 connected with the second pivot member 21. The second tube 20 has a passage 200 defined therethrough. A slot 201 is longitudinally defined through a wall of the second tube 20 and communicates with the passage 200. A tubular member 211 is extended from the second pivot member 21 and has a reception hole 210 in which the axle 111 of the first pivot member 11 is inserted. The second pivot member 21 includes an insertion hole 212 corresponding to the aperture 113. The operation unit 4 has a sleeve 40 which has a sleeve hole 401. The tubular member 211 of the second pivot member 21 is rotatably inserted into the sleeve hole 401 of the sleeve 40, and the axle 111 of the first pivot member 11 is rotatably inserted into the reception hole 210 of the second pivot member 21. A first arm 41 and a second arm 42 are extended radially from the sleeve 40 in two different angles. The first arm 41 has a first fixed end 411 at a distal end thereof. The operation unit 4 further includes a pulling member 43 and an operation member 44. A first end of the pulling member 43 is fixed with the first fixed end 411 of the first arm 41 and a second end of the pulling member 43 is extended through the passage 200 to connect with the operation member 44 which is movably engaged with the slot 201. The second arm 42 has a second fixed end 421 at a distal end thereof and the second fixed end 421 has a through hole. The pulling member 43 may be a cable or a rod. The operation member 44 may be a plate, a lever, etc. The locking unit 3 has a pin 31 and an elastic member 34. One end of the pin 31 includes a shank 310 having a fixing end 312 and the other end of the pin 31 includes a head having a curved surface 311. The elastic member 34 is sleeved on the shank 310. The pin 31 passes through the aperture 113 of the first pivot member 11, the insertion hole 212 of the second pivot member 21 and the through hole of the second fixed end 421 of the second arm 42. The fixing end 312 of the pin 31 includes threads which are threadedly connected with a nut 3120 to fix the pin 31 to the second fixed end 421 of the operation unit 4. The elastic member 34 is a spring. A casing 99 may be mounted to cover the first pivot unit 1, the second pivot unit 2, the locking unit 3 and the operation unit 4 as shown in FIG. 5.

Figure 4:
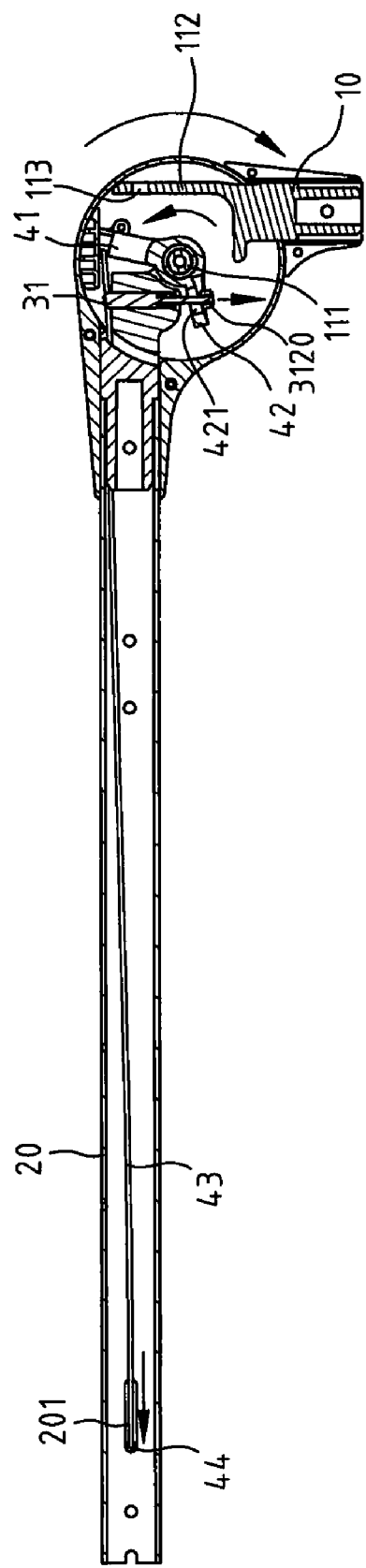
FIG. 4 is a cross sectional view showing the operation of the folding mechanism according to the present invention.

Referring to FIGS. 2 to 5, the folding mechanism for the joint according to the present invention is used on a baby stroller 9. When the user wants to fold the baby stroller 9, he or she moves the operation member 44 along the slot 201 and the pulling member 43 connected with the operation member 44 pulls the first arm 41 of the operating unit 4. The first and second arms 41, 42 rotate an angle and a central axis of the sleeve 40 is the rotating axis. The pin 31 connected with the second arm 42 is moved downward with the second arm 42, and therefore the pin 31 is disengaged from the aperture 113. In the mean time, the elastic member 34 received in the insertion hole 212 of the second pivot member 21 is compressed. As shown in FIG. 4, the first and second pivot units 1, 2 are no longer fixed by the locking unit 3, and are pivoted about the central axis of the sleeve 40. Thus, the baby stroller 9 is folded. Then, the pin 31 is pushed by the elastic member 34 and moved along the insertion hole 212 to the original state. When unfolding the baby stroller 9, the first and second pivot units 1, 2 are pivoted to allow the aperture 113 and the insertion hole 212 to be in alignment with each other. The curved surface 311 of the head of the pin 31 moves along the frame 112 until the elastic member 34 pushes the pin 31 into the aperture 113 to lock the first and second pivot units 1, 2. Then, the baby stroller 9 is unfolded and set.

A conventional operation member is located close to the joint. Referring to FIG. 5, the operation member 44 according to the present invention is located close to the handle of the baby stroller 9. Therefore, the user do not need to bend over to operate the operation member 44 and can easily handle the operation member 44. Furthermore, the operation member 44 is out of the reach of the baby, which preventing the baby from accidentally folding the baby stroller 9.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A folding mechanism for a joint, comprising:
   a first pivot unit including a first tube connected with a first pivot member, the first pivot member having an axle and a frame extended therefrom, the frame having an aperture;
   a second pivot unit including a second tube connected with a second pivot member, the second tube having a passage defined longitudinally therethrough and a slot defined through a wall of the second tube and communicating with the passage, a tubular member connected to the second pivot member and having a reception hole in which the axle is inserted, the second pivot member having an insertion hole corresponding to the aperture;
   a locking unit including a pin which includes a shank having a fixing end, an elastic member mounted to the shank and the pin extending through the aperture and the insertion hole; and
   an operation unit including a sleeve having a sleeve hole in which the tubular member is rotatably inserted, the sleeve having a first arm and a second arm extending radially therefrom in two different angles, the first arm having a first fixed end at a distal end thereof and a pulling member having a first end thereof fixed with the first fixed end, a second end of the pulling member extending through the passage and connected with an operation member which is movably engaged with the slot, the second arm having a second fixed end at a distal end thereof and the fixing end of the pin fixed to the second fixed end of the second arm; wherein the pin is selectively disengaged from the aperture by movement of the operation member within the slot, thereby allowing the first pivot member to pivot with respect to the second pivot member.

2. The folding mechanism as claimed in claim 1, wherein the pulling member is a cable.

3. The folding mechanism as claimed in claim 1, wherein the pulling member is a rod.

4. The folding mechanism as claimed in claim 1, wherein the operation member is a plate.

5. The folding mechanism as claimed in claim 1, wherein the operation member is a lever.

6. The folding mechanism as claimed in claim 1, wherein the elastic member is a spring.

7. The folding mechanism as claimed in claim 1, wherein the pin includes a curved surface at an end opposite to the fixing end.

8. The folding mechanism as claimed in claim 1, wherein the fixing end of the pin includes threads which are threadedly connected with a nut to fix the pin to the second fixed end of the operation unit.

9. The folding mechanism as claimed in claim 1, wherein a casing is mounted to cover the first pivot unit, the second pivot unit, the locking unit and the operation unit.

* * * * *